Sept. 25, 1951 E. S. BOERNER Plant Pat. 1,040
ROSE PLANT
Filed July 18, 1950
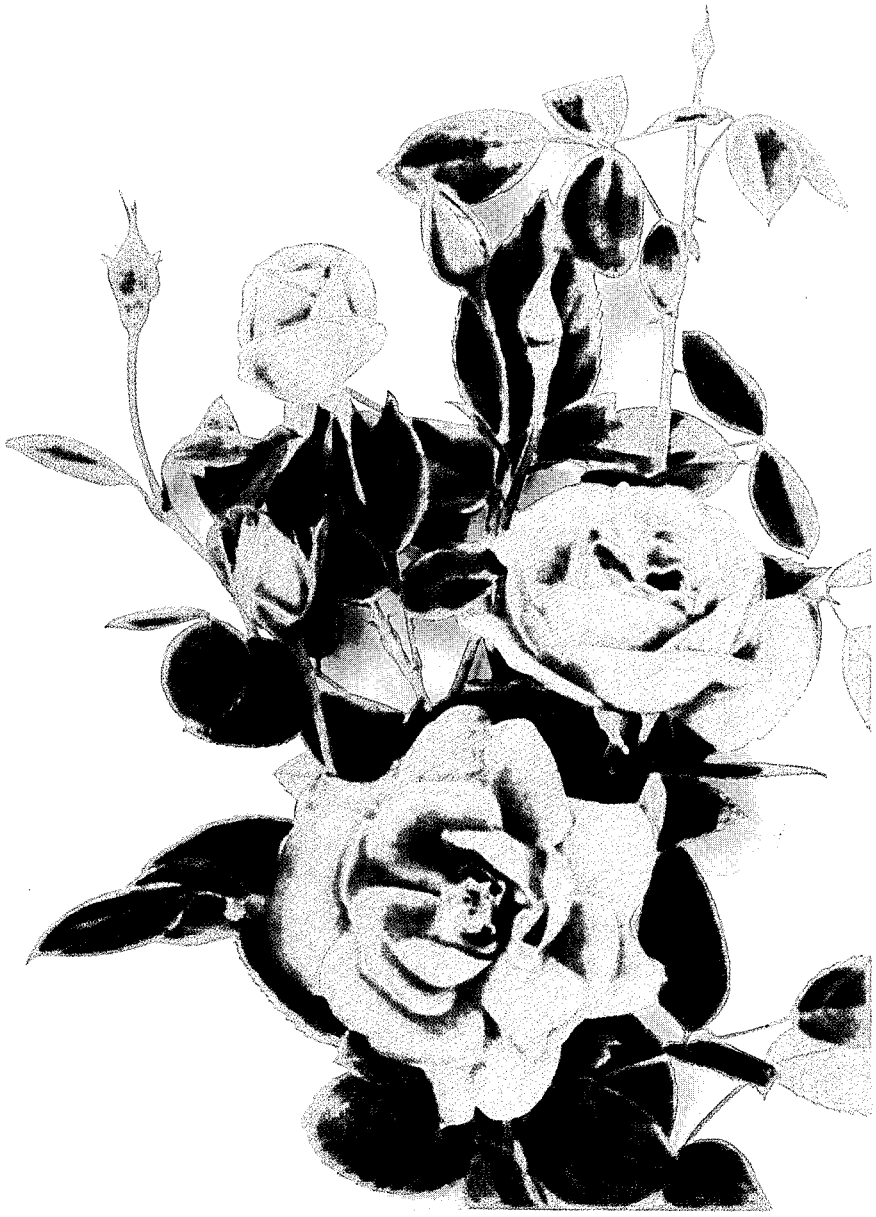
Inventor.
E. S. Boerner
By: Robert Cobb
Attorneys.

Patented Sept. 25, 1951

Plant Pat. 1,040

UNITED STATES PATENT OFFICE 1,040

ROSE PLANT

Eugene S. Boerner, Newark, N. Y., assignor to Jackson & Perkins Company, Newark, N. Y., a corporation of New York Application July 18, 1950, Serial No. 174,554

1 Claim. (Cl. 47—61)

The present invention relates to a new and distinct variety of floribunda rose plant of the so-called Park type, originated by crossing an unnamed sport of the variety "Lilette Mallerin" (unpatented) × an unnamed and unpatented red floribunda seedling.

The primary objective of this cross was to obtain an improved Park type of a floribunda rose, and this objective was effectively fulfilled by the fact that this new variety is quite distinctive from the floribundas produced in the past, as well as from any other rose variety of which I am aware.

Among the outstanding features which distinguish this new variety from others are the following:

(1) It is taller in its habit of growth, and may be said to be almost a shrub, which is quite different from the habit of growth of the usual floribundas such as "World's Fair" (Plant Patent No. 362);

(2) The Pomegranate Purple overcast with Tyrian Rose color of the flowers of the new variety is unique and unusual for any kind of rose;

(3) The showiness of the blooms of the aforementioned color in this type of rose, combined with its continuity of bloom, makes the new variety exceptional;

(4) The color of the stamens is very unusual in that the center is Carmine, and edged with Buff-Yellow.

Asexual reproduction of the new variety by budding at Newark, New York, and at Pleasanton, California, shows that the foregoing characteristics come true to form and are established and transmitted through succeeding propagations.

The accompanying drawing shows specimens of the new variety, with the foliage and flowers in different stages of development.

The following is a detailed description of the new variety, with color terminology in accordance with Ridgway's Color Standards and Nomenclature:

Parentage: Seedling.

*Seed parent.*—Unnamed sport of "Lilette Mallerin".

*Pollen parent.*—Unnamed red floribunda seedling.

Classification:

*Botanic.*—Large-flowered polyantha.

*Commercial.*—Park type of floribunda rose.

*Flower*

(Observations made in the greenhouse at Newark, New York, in the morning of April 15, 1950.)

Blooming habit: Recurrent—continuous.

Bud:

*Size.*—Medium.

*Form.*—Ovoid. Is not affected by wet or hot weather.

*Color.*—When sepals first divide—Victoria Lake, Plate 1. When petals begin to unfurl—Oxblood Red, Plate 1. When half blown—inside of petals—between Oxblood Red, Plate 1, and Carmine, Plate 1. Reverse of petals—Pomegranate Purple, Plate 12.

*Sepals.*—Slightly branched. Curl back when petals begin to unfurl. Color—inside: Absinthe Green, Plate 31; outside: Kildare Green, Plate 31.

*Calyx.*—Shape—pear. Size—small. Aspect—smooth. Odor when rubbed—none. Color—Lettuce Green, Plate 5.

*Peduncle.* — Length — medium. Aspect—smooth. Color—Lettuce Green, Plate 5. Strength—bending; slender.

*Opening.*—Bud opens up well. Is not affected by adverse weather conditions.

Bloom:

*Size.*—Medium. Average size when fully expanded, 3 inches to 3½ inches.

*Borne.*—Singly and several together.

*Stems.*—Medium length; normal strength.

*Form.*—When first open—high center. Permanence—retains its form to the end.

*Petalage.*—Double (full but open center). Number of petals under normal conditions, 15 to 20.

*Color.*—Center of flower—Pomegranate Purple, Plate 12. Outer petals—Pomegranate Purple, Plate 12, slightly overcast with Tyrian Rose, Plate 12. Base of petals (aiglet)—Sulphur Yellow, Plate 5. Inside of petals—Pomegranate Purple, Plate 12, overcast with Tyrian Rose, Plate 12. Reverse of petals—Spinel Red, Plate 26, lightly overcast with Tyrian Rose, Plate 12. General tonality from a distance—Pomegranate Purple, Plate 12.

*Discoloration.*—General tonality at end of first day—Pomegranate Purple, Plate 12. Second day—Pomegranate Purple, Plate 12, overcast with Tyrian Rose, Plate 12. Third day—Pomegranate Purple, Plate 12, lightly overcast with Tyrian Rose, Plate 12.

Petals:

*Texture.*—Thick. Is not affected by wet or hot weather.

*Appearance.* — Inside — velvety. Outside — satiny.

1

*Form.*—Oval, slightly notched.

*Arrangement.*—Informal (with "rags" in center). Petaloids in center—few; large.

*Persistence.*—Drop off cleanly.

*Fragrance.*—Moderate. Nature—"Old Rose perfume" (centifolia).

*Lasting quality.*—On the plant and as cut flower—long.

Genital organs:

*Stamens, anthers.*—Medium size; many. Color—Carmine center, Plate 1, edged Buff-Yellow, Plate 4. Arrangement—regular around styles.

*Stamens, filaments (threads).*—Medium length. Color—Carmine, Plate 1.

*Pollen.*—Color—Maize Yellow, Plate 4.

*Styles.*—Loosely separated; uneven length; short; thin.

*Stigmas.*—Color—Pale Orange Yellow, Plate 3.

*Ovaries.*—All enclosed in calyx.

*Plant*

Form: Bush

Growth: Vigorous; upright; branching.

Foliage: 5 leaflets.

*Size.*—Medium.

*Quantity.*—Normal.

*Color.*—New foliage—upper side: Yellowish Oil Green, Plate 5; serrations Oxblood Red, Plate 1; under side: Oil Green, Plate 5, lightly overcast with Oxblood Red, Plate 1; serrations Oxblood Red, Plate 1. Old foliage—upper side: Spinach Green, Plate 5; under side: Light Hellebore Green, Plate 17.

2

*Shape.*—Oval pointed.

*Texture.*—Upper side—leathery; glossy. Under side—smooth. Ribs and veins—ordinary.

*Edge.*—Serrated (saw toothed).

*Serration.*—Single; small.

*Leaf stem.*—Color—Lettuce Green, Plate 5. Under side—prickles.

*Stipules.*—Short; smooth.

*Disease resistance.*—Resistant.

Wood:

*New wood.*—Color—Light Elm Green, Plate 17. Bark—smooth.

*Old wood.*—Color—Forest Green, Plate 17. Bark—smooth.

Thorns:

*Thorns.*—Quantity—on main stalks from base and on laterals from stalk—ordinary. Form—narrow base; medium length; hooked downward. Color when young—Yellowish Oil Green, Plate 5, with slight cast of Spectrum Red, Plate 1. Position—irregular.

*Prickles and short needles.*—None.

I claim:

A new and distinct variety of floribunda rose plant of the Park type, characterized as to novelty by its tall and shrub-like habit of growth, by its showiness and continuity of blooms of Pomegranate Purple overcast with Tyrian Rose color, and by the Carmine color of the center stamens edged with Buff-Yellow, substantially as shown and described.

EUGENE S. BOERNER.

No references cited.